(12) United States Patent
Kunos et al.

(10) Patent No.: US 8,293,724 B2
(45) Date of Patent: Oct. 23, 2012

(54) THERAPEUTIC APPLICATIONS OF FATTY ACID AMIDE HYDROLASE INHIBITORS

(75) Inventors: George Kunos, Bethesda, MD (US); Alexandros Makriyannis, Watertown, MA (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 208 days.

(21) Appl. No.: 12/755,227

(22) Filed: Apr. 6, 2010

(65) Prior Publication Data

US 2010/0261674 A1    Oct. 14, 2010

Related U.S. Application Data

(63) Continuation-in-part of application No. PCT/US2008/011657, filed on Oct. 10, 2008.

(60) Provisional application No. 60/998,661, filed on Oct. 12, 2007.

(51) Int. Cl.
*A61K 31/69* (2006.01)
*A61K 31/10* (2006.01)
*A61K 317/06* (2006.01)
*C07F 5/02* (2006.01)
*C07F 9/02* (2006.01)

(52) U.S. Cl. .......... 514/64; 514/139; 514/679; 514/709; 568/6; 568/29; 558/202

(58) Field of Classification Search ................ 568/6, 29; 558/202; 514/64, 139, 678
See application file for complete search history.

(56) References Cited

U.S. PATENT DOCUMENTS

| | | | |
|---|---|---|---|
| 4,933,367 A | 6/1990 | Wolff et al. | |
| 6,462,054 B1 | 10/2002 | Boger | |
| 6,562,846 B2 | 5/2003 | Sit et al. | |
| 2005/0203067 A1 | 9/2005 | Hresko et al. | |

FOREIGN PATENT DOCUMENTS

| | | |
|---|---|---|
| EP | 0 020 161 A2 | 12/1980 |
| WO | WO 2004/103040 A2 | 12/2004 |
| WO | WO 2008/013963 A2 | 1/2008 |

OTHER PUBLICATIONS

Ghomashchi et al. Trifluoromethyl ketones and methyl fluorophosphonates as inhibitors of group IV and VI phospholipases A2: structure-function studies with vesicle, micelle, and membrane assays. Biochimica et Biophysica Acta 1420, (1999), 45-56.*

Lapeyre et al. Design, Synthesis, and Evaluation of Pharmacological Properties of Cinnamic Derivatives as Antiatherogenic Agents. Journal of Medicinal Chemistry, (2005), vol. 48, 8115-8124.*

Boger et al., "Trifluoromethyl Ketone Inhibitors of Fatty Acid Amide Hydrolase: A Probe of Structural and Conformational Features Contributing to Inhibition," *Bioorganic & Medicinal Chemistry Letters* 9:265-270, 1999.

Calandra et al., "Fluorophosphoramide-Containing Peptide Analogs as Irreversible Peptidase Inhibitors," *Peptides Structure and Function* Proceedings of the Ninth American Peptide Symposium (Deber, Hruby and Kopple eds.), Pierce Chemical Company, Rockford, Illinois, 9:802-806, 1985.

Khodair et al., "Synthesis of Sulphones from Sulphonyl Fluorides and Organometallic Compounds," *Zeitschrift für Naturforschung* 338(4):403-406, 1978.

Siewiński et al., "Phenylalkylsulfonyl Derivatives as Covalent Inhibitors of Penicillin Amidase," *Hoppe-Seyler's Z. Physiol. Chem.* 365(8):829-837, Aug. 1984.

Truce et al., "Friedel-Crafts Cyclization of ω-Phenylalkanesulfonyl Chlorides," *Journal of American Chemical Society* 74(4):974-977, 1952.

Vara Prasad et al., "Synthesis and structure-activity studies of novel benzocycloheptanone oxazolidinone antibacterial agents," *Bioorganic & Medicinal Chemistry Letters* 16:5392-5397, 2006.

International Search Report dated Mar. 9, 2009, from International Application No. PCT/US2008/011657.

\* cited by examiner

*Primary Examiner* — Sikarl Witherspoon
(74) *Attorney, Agent, or Firm* — Klarquist Sparkman, LLP

(57) ABSTRACT

Fatty acid amide hydrolase (FAAH) is an enzyme responsible for the degradation of oleamide (an endogenous sleep-inducing lipid) and anandamide (an endogenous ligand for cannabinoid receptors). Disclosed herein are potent inhibitors of FAAH and methods for their use for treating a variety of disorder, including hypertension and cardiac hypertrophy.

14 Claims, 8 Drawing Sheets

THERAPEUTIC APPLICATIONS OF FATTY ACID AMIDE HYDROLASE INHIBITORS

CROSS REFERENCE TO RELATED APPLICATION

This application is a continuation-in-part of International Application No. PCT/US2008/011657, filed Oct. 10, 2008, which, in turn, claims the benefit of the earlier filing date of U.S. provisional application No. 60/998,661, filed Oct. 12, 2007, both of which are incorporated in their entirety herein by reference.

FIELD

This disclosure concerns novel inhibitors of fatty acid amide hydrolase (FAAH) and methods for their use. Disclosed herein are potent inhibitors of FAAH and methods for their use for treating a variety of disorders, including hypertension and cardiac hypertrophy.

BACKGROUND

Cannabinoids, including marijuana's main psychoactive ingredient, $\Delta^9$-tetrahydrocannabinol (THC), are known to have cardiovascular effects, an important component of which is a decrease in arterial blood pressure (hypotension). The endogenous cannabinoid anandamide also elicits hypotension, which is mediated by the $CB_1$ cannabinoid receptor, the same receptor that mediates the psychotropic effects of marijuana and THC. Indeed, efforts to develop synthetic cannabinoid analogs as antihypertensive agents have been hampered by the fact that the psychotropic and hypotensive actions could not be separated. Because $CB_1$ receptors in the brain mediate the psychological effects of marijuana, treating a chronic disease with a drug that directly stimulates $CB_1$ receptors may be unacceptable.

U.S. Pat. No. 6,562,846 to Sit et al. (Sit) discloses compounds and pharmaceutical compositions purported to be useful for inhibiting FAAH. Sit proposes that inhibitors of FAAH can be used to increase the levels of endogenous cannabinoids and Sit proposes that such an increase in endogenous cannabinoids may be useful for treating certain disorders.

The FAAH inhibitors described by Sit generally are bisarylimidazole derivatives. One specific example has the formula:

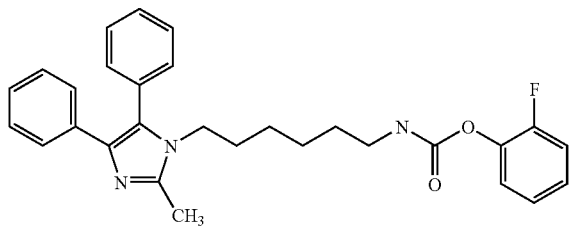

U.S. Pat. No. 6,462,054 to Boger describes FAAH inhibitors having an α-keto heterocyclic group. A typical representative of Boger's inhibitors is the α-keto oxazolopyridine derivative of oleic acid:

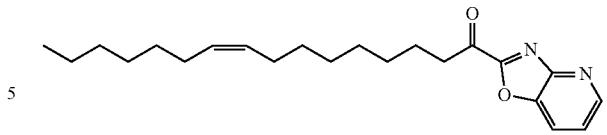

Boger proposes that such compounds can be used to treat sleep disorders, such as by inducing sleep. However, previously proposed FAAH inhibitors, including those proposed by Boger, lack in vivo activity despite exhibiting inhibition of FAAH in vitro. Therefore, there is a need for new FAAH inhibitors having in vivo activity.

SUMMARY

Disclosed herein are novel FAAH inhibitors. In one embodiment the inhibitors are represented by the formula Ar—R-E wherein Ar is an optionally substituted aryl or heteroaryl group;
R is an aliphatic linker group; and
E is an electrophilic moiety capable of reversibly or irreversibly interacting with an FAAH active site nucleophile.

In one aspect, disclosed is a method for treating anxiety, an anxiety disorder, or a psychological disorder associated with anxiety by administering an FAAH inhibitor to a subject having one or more of such conditions. In another aspect the disclosed compounds are used to treat cardiovascular disorders, such as hypertension or cardiac hypertrophy by reducing cardiac contractility. In certain embodiments the disclosed compounds have analgesic and/or soporific activity. In still another aspect the disclosed compounds can be used to treat glaucoma. Exemplary FAAH inhibitors disclosed herein have in vivo efficacy in addition to in vitro activity, thus permitting the treatment of intact subjects.

The foregoing and other objects, features, and advantages of the invention will become more apparent from the following detailed description, which proceeds with reference to the accompanying figures.

DETAILED DESCRIPTION

I. Introduction

Figure 1:
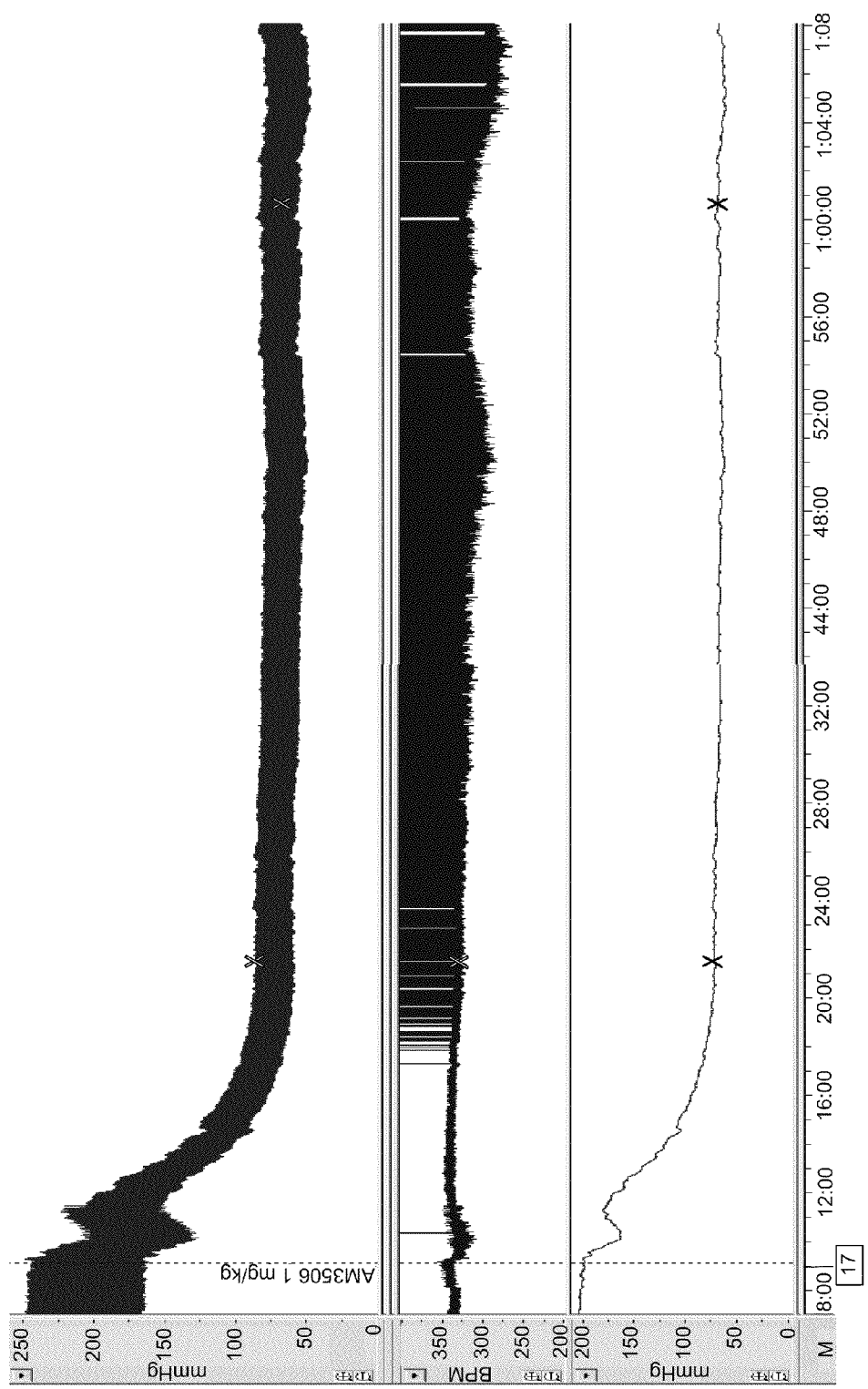
FIG. 1 is a chart illustrating the hypotensive effect of AM3506 (administered intravenously 1 mg/kg in 50 µl) in an anesthetized spontaneously hypertensive rat (SHR); tracings (from top to bottom) represent phasic blood pressure, heart rate and mean blood pressure.
Figure 2:
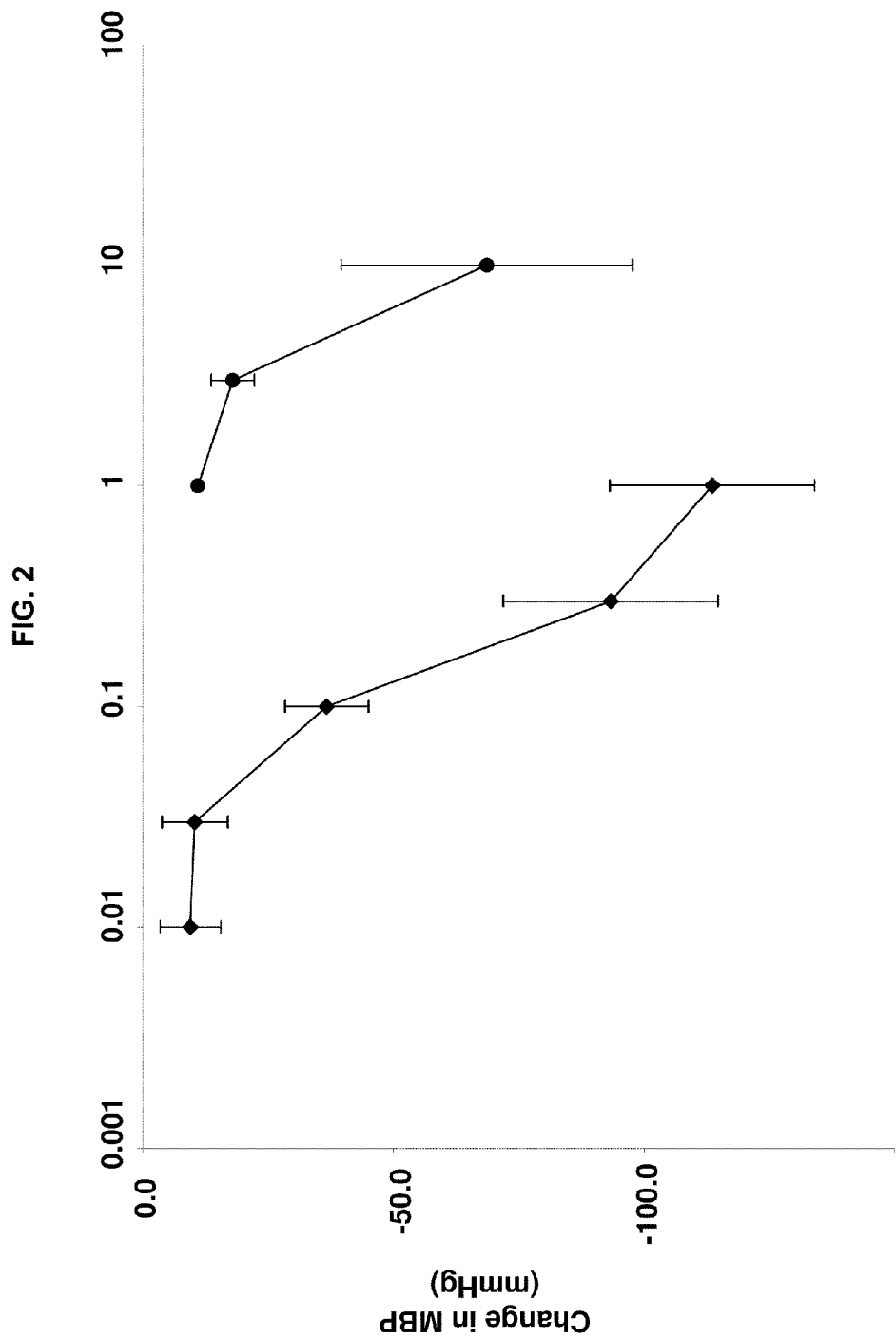
FIG. 2 is a graph illustrating the dose-dependent hypotensive effect of both URB597 and the disclosed FAAH inhibitor AM3506 (mean blood pressure versus dosage in mg/kg intravenously; points and bars represent mean+/−SE, n=4 for both compounds), highlighting that AM3506 is about ten times more potent than URB597, i.e., causes equivalent hypotension at ten times lower doses.

Endogenous cannabinoids are recently discovered lipid-like substances produced in the brain and peripheral tissues that bind to and activate cannabinoid receptors present in the cell membrane and elicit effects similar to those caused by marijuana. Once released from the cell, the endogenous cannabinoid anandamide is degraded by the enzyme FAAH. Similar to marijuana, anandamide can lower blood pressure and can induce hypotension. Disclosed herein are compounds that inhibit the degradation of anandamide by inhibiting FAAH. Also disclosed are compositions containing FAAH inhibitors and methods for using such compounds and compositions to treat several disorders, including, without limitation cardiovascular disorders, such as hypertension.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B.

Anxiety is a state of fearfulness that is unprovoked by an environmental threat or is disproportionate to an environmental threat. Anxiety may be acute and short term lasting hours to days; or chronic and lasting from many days to weeks or longer.

The term "clinical anxiety" refers to any form of anxiety for which treatment is necessary or indicated in order to alleviate it. Such clinical anxiety may be persistent or recurrent and typically severe.

Anxiety disorders include, but are not limited to, any of the anxiety disorders as provided in the Diagnostic and Statistical Manual of Mental Disorders, Fourth Edition. (Copyright 1994 American Psychiatric Association). Such disorders include, but are not limited to, panic disorder, agoraphobia, generalized anxiety disorder, specific phobia, social phobia, obsessive-compulsive disorder, acute stress disorder, and post-traumatic stress disorder; and adjustment disorders with anxious features, anxiety disorders due to general medical conditions, substance-induced anxiety disorders, and the residual category of anxiety disorder not otherwise specified. An anxiety disorder may be accompanied by tachycardia or dyspnea.

Variables such as $R^1$, $R^2$, $R^3$, $R^4$, $R^6$, $R^7$, $R^8$, $R^9$, $R^{10}$, $R^{11}$, X and Y used throughout the disclosure are the same variables as previously defined unless stated to the contrary.

"Optional" or "optionally" means that the subsequently described event or circumstance can but need not occur, and that the description includes instances where said event or circumstance occurs and instances where it does not.

"Derivative" refers to a compound or portion of a compound that is derived from or is theoretically derivable from a parent compound.

The term "subject" includes both human and veterinary subjects.

The term "aliphatic group" is defined as including alkyl, alkenyl, alkynyl, halogenated alkyl and cycloalkyl groups as described above. A "lower aliphatic" group is a branched or unbranched aliphatic group having from 1 to 10 carbon atoms.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched aliphatic hydrocarbon having from 1 to 10 carbon atoms.

The term "aryl group" refers to any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted. The term "alkyl amino" refers to alkyl groups as defined above where at least one hydrogen atom is replaced with an amino group.

The term "hydroxyl group" is represented by the formula —OH. The term "alkoxy group" is represented by the formula —OR, where R can be an alkyl group, optionally substituted with an alkenyl, alkynyl, aryl, aralkyl, cycloalkyl, halogenated alkyl, or heterocycloalkyl group as described above.

The term "hydroxyalkyl group" refers to an alkyl group that has at least one hydrogen atom substituted with a hydroxyl group. The term "alkoxyalkyl group" is defined as an alkyl group that has at least one hydrogen atom substituted with an alkoxy group described above. Where applicable, the alkyl portion of a hydroxyalkyl group or an alkoxyalkyl group can have aryl, aralkyl, halogen, hydroxy and/or alkoxy substituents.

The term "amine group" is represented by the formula —NRR', where R and R' can be, independently, hydrogen or an alkyl, alkenyl, alkynyl, aryl, aralkyl, cycloalkyl, halogenated alkyl, or heterocycloalkyl group described above.

The term "amide group" is represented by the formula —C(O)NRR', where R and R' independently can be a hydrogen, alkyl, alkenyl, alkynyl, aryl, aralkyl, cycloalkyl, halogenated alkyl, or heterocycloalkyl group described above.

The term "aralkyl" refers to an aryl group having an alkyl group, as defined above, attached to the aryl group. Examples aralkyl groups include, without limitation, benzyl groups and trityl groups.

The terms "halogenated alkyl" or "haloalkyl group" refer to an alkyl group as defined above with one or more hydrogen atoms present on these groups substituted with a halogen (F, Cl, Br, I).

Optionally substituted groups, such as "substituted alkyl," refers to groups, such as an alkyl group, having from 1-5 substituents, typically from 1-3 substituents, selected from alkoxy, optionally substituted alkoxy, acyl, acylamino, acyloxy, amino, aminoacyl, aminoacyloxy, aryl, carboxyalkyl, optionally substituted cycloalkyl, optionally substituted cycloalkenyl, optionally substituted heteroaryl, optionally substituted heterocyclyl, hydroxy, thiol and thioalkoxy.

Certain compounds disclosed herein may be isolated or formulated as solvates. "Solvate" refers to a compound physically associated with one or more solvent molecules. This physical association involves varying degrees of ionic and covalent bonding, including by way of example covalent adducts and hydrogen bonded solvates. In certain instances the solvate will be capable of isolation, for example when one or more solvent molecules are incorporated in the crystal lattice of the crystalline solid. "Solvate" encompasses both solution-phase and isolable solvates. Representative solvates include ethanol associated compounds, methanol associated compounds, and the like. "Hydrate" is a solvate wherein the solvent molecule(s) is/are $H_2O$.

It is understood that substituents and substitution patterns of the compounds described herein can be selected by one of ordinary skill in the art to provide compounds that are chemically stable and that can be readily synthesized by techniques known in the art and further by the methods set forth in this disclosure. Reference will now be made in detail to the present preferred embodiments.

II. Compounds and Compositions

Disclosed herein are compounds that inhibit FAAH and compositions containing such compounds. In one embodiment disclosed FAAH inhibitory compounds have formula Ar—R-E wherein Ar is an optionally substituted aryl or heteroaryl group;

R is an aliphatic linker group; and

E is an electrophilic moiety capable of reversibly or irreversibly interacting with an FAAH active site nucleophile.

With reference to the formula above, the electrophilic moiety E may include one or more electrophilic groups, such as trifluoromethyl ketones, boronic acids, boronic acid esters, fluorosulfones, fluorophosphonates, α-haloketones and α-ketoesters. In one embodiment, E is a moiety capable forming a covalent bond with an FAAH active site nucleophile; such inhibitors, when they react irreversibly with an enzyme are commonly referred to as mechanism-based or "suicide" inhibitors.

In particular embodiments, E represents a fluorosulfone or fluorophosphonate moiety. Such compounds have the formula

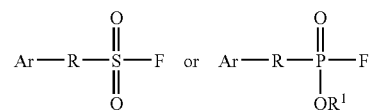

wherein R represents $(CH_2)_n$ and n is from 2 to 20, such as from 2 to 10, or from 3 to 7. $R^1$ represents H or a lower alkyl group. Where $R^1$ represents H, typically the compound will be isolated in its salt form, for example, having the formula

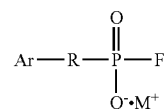

wherein $M^+$ represents a pharmaceutically acceptable counterion.

With continued reference to the general formula, Ar represents an optionally substituted aryl group.

Examples of such Ar groups in the above general formula can be represented by the formula

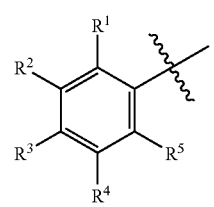

wherein $R^1$, $R^2$, $R^3$, $R^4$ and $R^5$ are, for each occurrence selected from H, —$OR^1$, —$NR^2R^3$ and halogen or two of $R^1$, $R^2$, $R^3$, $R^4$ and $R^5$ together with the phenyl ring to which they are attached form a fused bicyclic ring system, optionally including one or more heteroatoms. Examples of such bicyclic ring systems include, without limitation, those represented by the formula

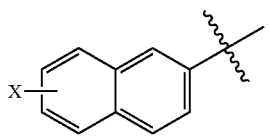

wherein X is selected from —OR⁶, —NR⁷R⁸ and halogen; and

R⁶, R⁷ and R⁸ are independently selected from H, lower alkyl, acyl and aralkyl

In one embodiment, Ar represents an optionally substituted phenyl ring, such as represented by the formula

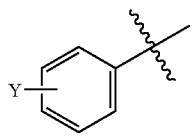

wherein Y is selected from —OR⁹, —NR¹⁰R¹¹ and halogen; and

R⁹, R¹⁰ and R¹¹ are independently selected from H, lower alkyl, acyl and aralkyl.

Exemplary fluorosulfonate FAAH inhibitors disclosed herein are represented by the formula

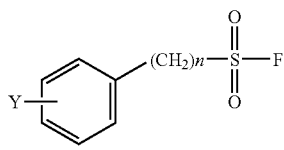

wherein Y is selected from —OR¹, NR²R³ and the halogens;

R¹, R² and R³ are independently selected from H, lower alkyl, acyl and aralkyl; and n is from about 2 to about 10, such as giving an alkyl linker of 2, 3, 4, 5, 6, 7, 8, 9 or 10 carbon atoms. In particular compounds, Y is —OR¹, and one example of such an FAAH inhibitor disclosed herein has the formula

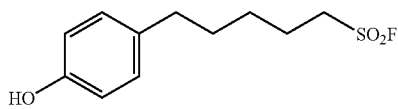

When compounds disclosed herein include an acidic function such as a carboxy group, or phosphonate group then suitable pharmaceutically acceptable cation counterions for the carboxy and phosphonate groups are well known to those skilled in the art and include alkaline, alkaline earth, ammonium, quaternary ammonium cations and the like. The terms "pharmaceutically acceptable salt" or "physiologically acceptable salt" refer to salts prepared by conventional means that include compounds including at least one acidic group that can form an acid-base salts with an inorganic or organic base. Examples of salts formed from inorganic bases include salts of the presently disclosed compounds with alkali metals such as potassium and sodium, alkaline earth metals, including calcium and magnesium and the like. Similarly, salts of acidic compounds with an organic base, such as an amine (as used herein terms that refer to amines should be understood to include their conjugate acids unless the context clearly indicates that the free amine is intended) are contemplated, including salts formed with basic amino acids, aliphatic amines, heterocyclic amines, aromatic amines, pyridines, guanidines and amidines. Of the aliphatic amines, the acyclic aliphatic amines, and cyclic and acyclic di- and tri-alkyl amines are particularly suitable for use in the disclosed compounds. In addition, quaternary ammonium counterions also can be used.

Particular examples of suitable amine bases (and their corresponding ammonium ions) for use in the present compounds include, without limitation, pyridine, N,N-dimethylaminopyridine, diazabicyclononane, diazabicycloundecene, N-methyl-N-ethylamine, diethylamine, triethylamine, diisopropylethylamine, mono-, bis- or tris-(2-hydroxyethyl)amine, 2-hydroxy-tert-butylamine, tris(hydroxymethyl)methylamine, N,N-dimethyl-N-(2-hydroxyethyl)amine, tri-(2-hydroxyethyl)amine and N-methyl-D-glucamine. For additional examples of "pharmaceutically acceptable salts," see Berge et al., *J. Pharm. Sci.* 66:1 (1977).

Compounds disclosed herein can be crystallized and can be provided in a single crystalline form or as a combination of different crystal polymorphs. As such, the compounds can be provided in one or more physical form, such as different crystal forms, crystalline, liquid crystalline or non-crystalline (amorphous) forms. Such different physical forms of the compounds can be prepared using, for example different solvents or different mixtures of solvents for recrystallization. Alternatively or additionally, different polymorphs can be prepared, for example, by performing recrystallizations at different temperatures and/or by altering cooling rates during recrystallization. The presence of polymorphs can be determined by X-ray crystallography, or in some cases by another spectroscopic technique, such as solid phase NMR spectroscopy, IR spectroscopy, or by differential scanning calorimetry.

In one embodiment the compounds disclosed herein have an inhibitory concentration ($K_i$) for FAAH of less than about 1 μM (1000 nM), such as from about 1 picomolar (0.001 nM) to about 500 nM. Preferred compounds have $K_i$ for FAAH of less than about 250 nM, such as from about 0.1 nM to about 100 nM and in particular from about 1 nM to about 50 nM. An exemplary FAAH inhibitor, AM3506 was found to have a $K_i$=31 nM for FAAH. In certain embodiments, the disclosed FAAH inhibitors are selective for FAAH, for example, as compared to other amidase or esterase enzymes, including, without limitation the neurotoxic esterase (NTE), acetylcholinesterase (ACHE) and/or monoacylglycerol lipase (MGL).

In one embodiment the disclosed FAAH inhibitors have an FAAH $K_i$ of from about 100 to about 10,000-fold lower than for another enzyme, such as MGL, for example from about 500 to about 5,000-fold lower, or from about 250 to about 1,000-fold lower. One FAAH inhibitor disclosed herein, has a $K_i$ for FAAH of 31 nM and a $K_i$=28,760 nM for MGL. Additionally, in certain embodiments, the disclosed FAAH inhibitors have a relatively low affinity for the $CB_1$ and/or $CB_2$ cannabinoid receptors. In such embodiments the FAAH inhibitors exert their effect on the $CB_1$ receptors indirectly, such as by inhibiting the degradation of endogenous or exogenously administered anandamide. Because $CB_1$ receptors in the brain mediate the psychological effects of marijuana, treating a chronic disease with a drug that directly stimulates $CB_1$ receptors may be unacceptable. However, inhibiting the degradation of the endogenous ligand for this receptor, anandamide, does not have the same effect or potential for abuse. In certain embodiments, the disclosed FAAH inhibitors may have a relative affinity for FAAH of from about two to about 10,000-fold less, and more particularly from about five to about 5,000-fold less, than for the $CB_1$ receptor the $CB_2$ receptor, or both. An exemplary FAAH inhibitor, AM3506, had a low affinity for the $CB_1$ cannabinoid receptor ($K_i$=192 nM) and a modest affinity for $CB_2$ ($K_i$=5,770 nM). Similarly, in certain examples the disclosed FAAH inhibitors do not significantly inhibit the anandamide transporter, for example AM3506 did not inhibit the anandamide transporter at concentrations of up to 20 µM. Thus in certain examples the disclosed FAAH inhibitors do not significantly inhibit anandamide uptake.

Another aspect of the disclosure includes pharmaceutical compositions prepared for administration to a subject and which include a therapeutically effective amount of one or more of the currently disclosed FAAH inhibitors. As used herein a "therapeutically effective amount" of a compound, can be the quantity of a compound which, when administered to an individual or animal, results in a discernible desired physiological effect in the individual or animal. The compounds described herein, and physiologically acceptable salts thereof, can have pharmacological properties when administered in therapeutically effective amounts for providing a physiological effect useful to treat a number of physiological conditions.

Typically, a "therapeutically effective amount" of a disclosed FAAH inhibitor is believed to range from about 5 mg/day to about 1,000 mg/day. The specific dosage level of active ingredient will depend upon a number of factors, including, for example, biological activity of the particular preparation, age, body weight, sex and general health of the individual being treated. Typically the dosage of a disclosed compound expressed on a mg/kg basis will be between about 0.01 mg/kg and 250 mg/kg of the subject's body weight, and more typically between about 0.05 mg/kg and 100 mg/kg, such as from about 0.2 to about 80 mg/kg, from about 5 to about 40 mg/kg or from about 1 to about 3 mg/kg of the subject's body weight. Thus, unit dosage forms can be formulated based upon the suitable ranges recited above and a subject's body weight.

Alternatively, dosages are calculated based on body surface area and from about 1 mg/m$^2$ to about 200 mg/m$^2$, such as from about 5 mg/m$^2$ to about 100 mg/m$^2$ will be administered to the subject per day. In particular embodiments administration of the therapeutically effective amount of the compound or compounds comprises administering to the subject from about 5 mg/m$^2$ to about 50 mg/m$^2$, such as from about 10 mg/m$^2$ to about 40 mg/m$^2$ per day. It is currently believed that a single dosage of the compound or compounds is suitable. However, a therapeutically effective dosage can be supplied over an extended period of time or in multiple doses per day. Thus, unit dosage forms also can be calculated using a subject's body surface area based on the suitable ranges recited above and the desired dosing schedule.

The therapeutically effective amount of a disclosed compound will depend on the route of administration, the species of subject and the physical characteristics of the subject being treated. Specific factors that can be taken into account include disease severity and stage, weight, diet and concurrent medications. The relationship of these factors to determining a therapeutically effective amount of the disclosed compounds is understood by those of skill in the art.

Pharmaceutical compositions for administration to a subject can include carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. Pharmaceutical formulations can include additional components, such as carriers. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the FAAH inhibitors herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In one aspect, disclosed methods include treating ocular disorders, such as glaucoma. Accordingly, embodiments of pharmaceutical compositions include those formulated for ophthalmic administration.

III. Methods for Using FAAH Inhibitors

Examples of the disclosed FAAH inhibitors are effective at treating cardiac disorders or pulmonary disorders. In particular, exemplary compounds are effective at reducing blood pressure in vivo, particularly in hypertensive subjects. In one embodiment a disclosed FAAH inhibitor reduces blood pressure in hypertensive subjects, but has little or substantially no effect on blood pressure in normotensive subjects. In another embodiment, the disclosed FAAH inhibitor does not elicit hyperglycemia and/or increase glucose intolerance in a subject.

In another aspect, the present disclosure provides a method of treating anxiety, an anxiety disorder, or a psychological disorder associated with anxiety by administering an inhibitor of FAAH to a subject having one or more of such conditions. In another embodiment, such a subject is not otherwise in need of treatment with an FAAH inhibitor. In one embodiment, the FAAH inhibitor is selective for FAAH as compared to the neurotoxic esterase (NTE) or acetylcholinesterase (ACHE).

In another embodiment, the FAAH inhibitor is formulated with an antianxiety compound which is not an FAAH inhibitor and/or administered as part of a combination therapy with such an antianxiety compound.

The disclosed FAAH inhibitors also are useful in the treatment of a variety of other neurological psychological disorders and conditions, including but not limited to pain, depression, attention deficit hyperactivity disorders, jet lag, insomnia, schizophrenia, pain, muscle spasticity, epilepsy, and seizure disorders as well as glaucoma.

In another aspect, disclosed are methods for increasing the levels of endogenous anandamide, endogenous oleoylethanolamide, and other endogenous fatty acid amides in a subject by administering a disclosed FAAH inhibitor to the subject. Similarly, the levels of an exogenously administered fatty acid amide, such as the blood, plasma, brain or other tissue concentrations of the fatty acid amide can be increased by administering a disclosed FAAH inhibitor.

EXAMPLES

The foregoing disclosure is further explained by the following non-limiting methods and examples.

General Methods and Materials

Anandamide, the $CB_1$ receptor antagonist AM251, and the anandamide transport inhibitors AM404 and OMDM-2 were obtained from Tocris; and the $CB_1$ antagonist SR141716 and the CB2 antagonist SR144528 were from the National Institute on Drug Abuse drug supply program. Drugs were mixed in corn oil and sonicated for 5 minutes at 4° C. The mixture was added to 4 parts of Pluronic F68 (Sigma-Aldrich) solution (40 mg/mL) dissolved in water and sonicated to obtain a stable suspension for bolus intravenous injections.

Rats were obtained from Harlan (Indianapolis, Ind.). Male, 8- to 10-month-old SHR, age-matched male Wistar-Kyoto rats (WKY), and 8- to 10-week-old male Sprague-Dawley rats were maintained on standard rat chow and water ad libitum. Dahl salt-sensitive and salt-resistant rats (male, Rapp strain, 6 weeks old) were maintained for 4 weeks on rat chow containing either 0.12% or 8% NaCl. Systolic blood pressure monitored daily by the tail-cuff technique was 120±11 mm Hg (salt-sensitive, 0.12% NaCl), 180±14 mm Hg (salt-sensitive, 8% NaCl), and 118±9 mm Hg (salt-resistant, 8% NaCl). Hypertension was induced in Sprague-Dawley rats by chronic infusion of angiotensin II (60 ng/min) via an osmotic minipump (Imig et al. *Hypertension* 2002; 39: 690-694. Rats were used 10 to 12 days after implantation of the minipump.

For hemodynamic measurements, rats were anesthetized with pentobarbital sodium (60 mg/kg IP) and tracheotomized to facilitate breathing. Animals were placed on controlled heating pads, and core temperature, measured via a rectal probe, was maintained at 37° C. A microtip pressure-volume catheter (SPR-838; Millar Instruments) was inserted into the right carotid artery and advanced into the left ventricle (LV) under pressure control as described previously. Polyethylene cannulae (P50) were inserted into the right femoral artery and vein for measurement of mean arterial pressure (MAP) and administration of drugs, respectively. After stabilization for 20 minutes, signals were continuously recorded with an ARIA pressure-volume conductance system (Millar) coupled to a Powerlab/4SP A/D converter (AD Instruments), stored, and displayed on a computer. Heart rate, maximal LV systolic pressure, MAP, and maximal slope of systolic pressure increment (+dP/dt) were computed with a cardiac pressure-volume analysis program (PVAN2.9; Millar). Cardiac output calculated and corrected according to in vitro and in vivo volume calibrations with PVAN2.918 was normalized to body weight (cardiac index [CI]). Total peripheral resistance index (TPRI) was calculated by the equation TPRI=MAP/CI. In 3 experiments, drugs were microinjected into the fourth cerebral ventricle as described by Ramirez-Gonzalez et al. *Circ Res.* 1983; 53, 150-157.

Time-dependent variables were analyzed by ANOVA followed by the Dunnett post hoc test. In other cases, the Student t test was used, as appropriate. Values with $P<0.05$ were considered statistically significant.

Synthetic Procedures and Physical Data

All chemicals were purchased from Aldrich Chemical Co. (Milwaukee, Wis.) and used without further purification unless otherwise specified.

Example 1

This example describes a general method for assaying FAAH inhibition by the disclosed compounds and determining their $IC_{50}$ values in vitro (Deutsch, D. G. and S. A. Chin, *Biochem. Pharmacol.* 46:791-796 (1993)). The indicated amount of each compound was preincubated in a buffer consisting of 300 µg of crude rat brain homogenate protein, 500 µg/ml fatty acid-free bovine serum albumin, in phosphate-buffered saline in a final volume of 1.0 ml, for 10 minutes at 37° C. Crude rat brain homogenate was obtained by decapitating female adult Sprague-Dawley rats, dissecting the desired tissue and homogenizing in five volumes of ice-cold TE (10 mM Tris-HCl, 1 mM EDTA, pH 7.6). Substrate (27.7 µg M anandamide+0.2 .mu.Ci of 221 Ci/mmol [$^3$H]anandamide ([arachidonyl-5,6,8,9,11,12,14,15-$^3$H]ethanolamide)) was then added and the samples incubated for 10 minutes. The reaction was quenched by the addition of chloroform:methanol (1:1) and enzyme activity was analyzed by TLC.

Figure 3:
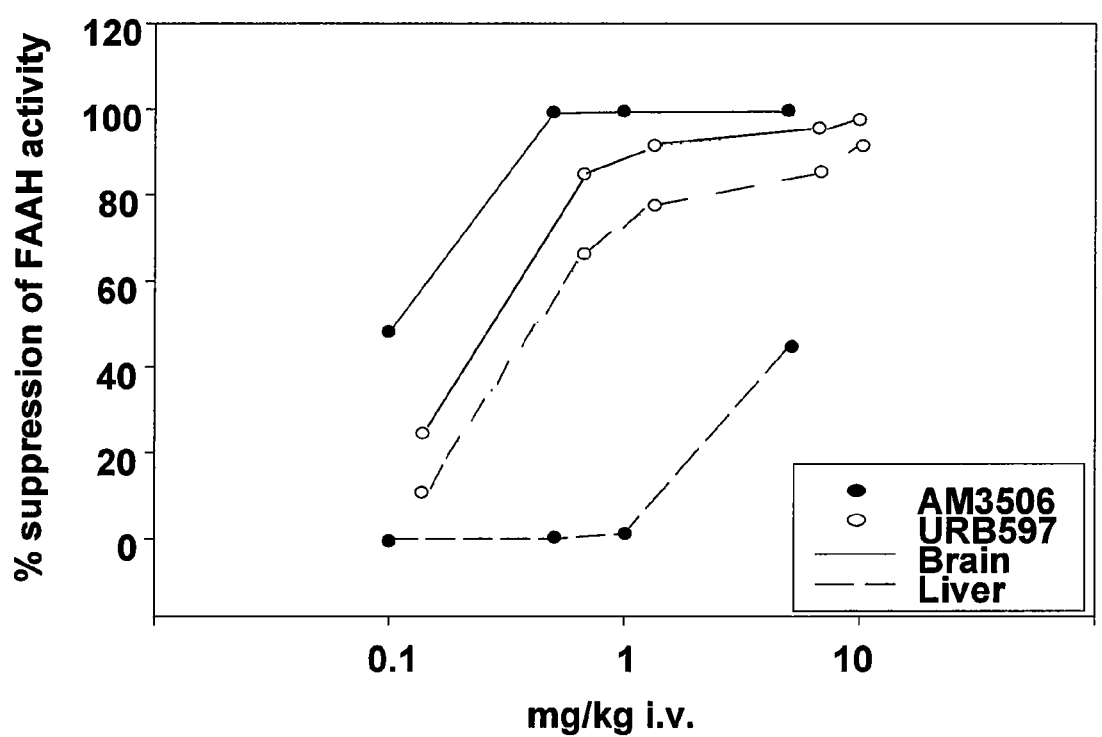
FIG. 3 is a graph illustrating the inhibition of FAAH activity in brain and liver, following in vivo administration of different doses of either URB597 or AM3506. The figure illustrates that in inhibiting FAAH activity, AM3506 is more potent than URB597 in the brain but much less potent than URB597 in the liver. A likely explanation for this is that AM3506 is rapidly metabolized in the liver before it can bind to and inhibit FAAH, whereas URB597 is less rapidly metabolized. The possible significance of this is that AM3506 treatment is less likely to cause fatty liver than URB597. The role of FAAH inhibition in fatty liver is suggested by a recent study in which feeding mice a high fat diet was shown to induce fatty livery, elevated hepatic anandamide levels due to decreased FAAH activity in the liver, and increased expression of CB1 cannabinoid receptors in the liver. Furthermore, mice lacking CB 1 cannabinoid receptors were resistant to high fat diet-induced fatty liver, which indicates that elevated levels of anandamide (due to its reduced degradation by FAAH) can lead to the development of fatty liver (see Osei-Hyiaman et al., *J. Clin. Invest.* 112:1296 (2005)). For example, at a dose of 0.3 mg/kg i.v., AM3506 lowers blood pressure in SHR by 90 mmHg (FIG. 2), and also causes 100% inhibition of FAAH in the brain but no inhibition (0%) in the liver (FIG. 3). A similar reduction of blood pressure is only achieved by 10 mg/kg URB597 (FIG. 2), which causes near complete inhibition of FAAH in brain but also >90% inhibition of FAAH in liver (FIG. 3). The latter will result in elevated levels of anandamide, which can lead to fatty liver, a potentially harmful condition that can lead to liver fibrosis and insulin resistance.
Figure 4A:
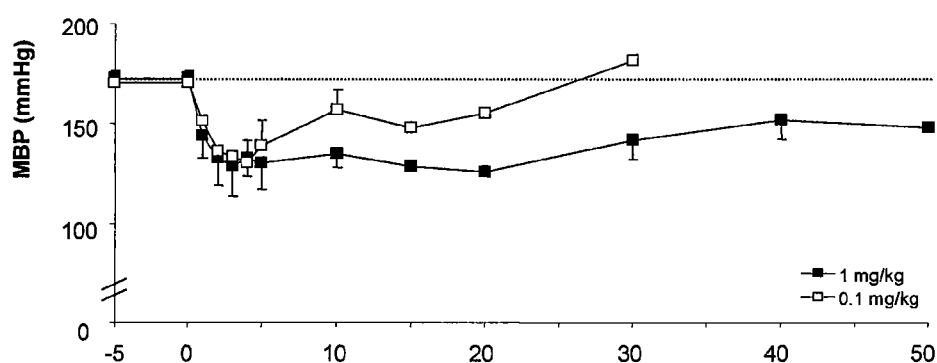
FIG. 4A is a graph of MBP in conscious SHR versus dosage of AM3506 demonstrating that the disclosed FAAH inhibitors decrease MBP, n=4.
Figure 4B:
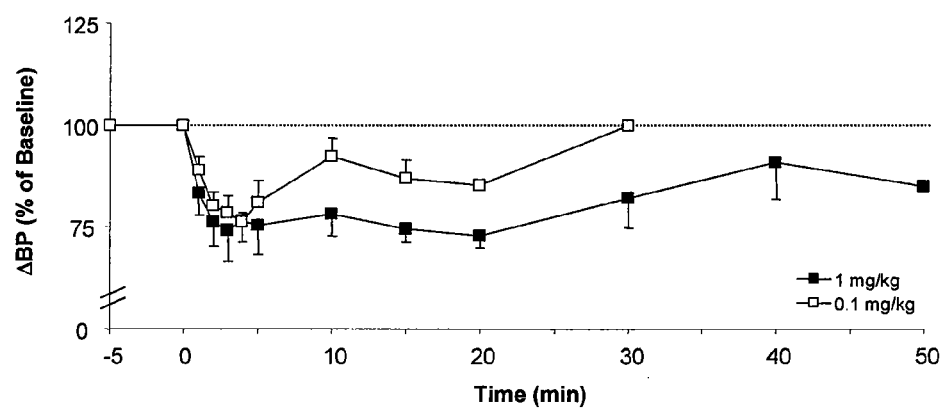
FIG. 4B is a graph of the change in blood pressure (ΔBP) as a percentage of baseline versus dosage of AM3506.
Figure 5A:
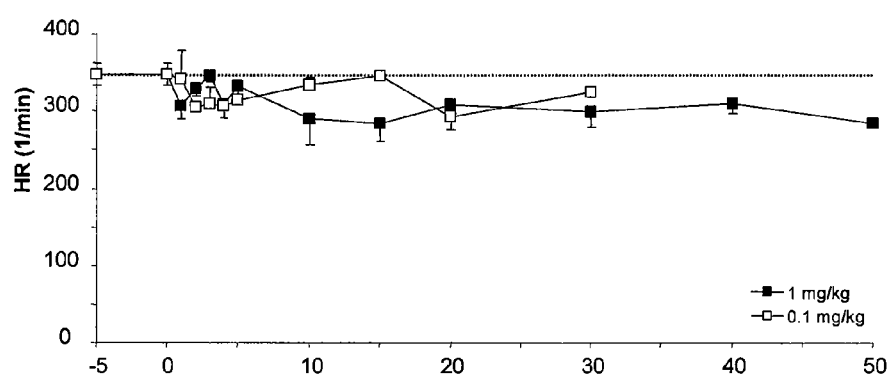
FIG. 5A is a graph of heart rate versus AM 3506 dosage, demonstrating that the disclosed FAAH inhibitors cause moderate bradycardia only at 1 mg/kg dose in conscious SHR rat (n=4).
Figure 5B:
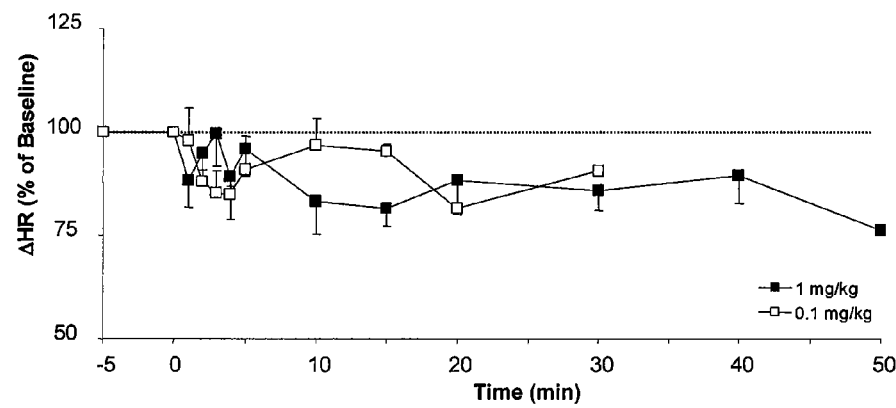
FIG. 5B is a graph of heart rate as a percentage of baseline versus AM 3506 dosage in conscious SHR rat (n=4).
Figure 6:
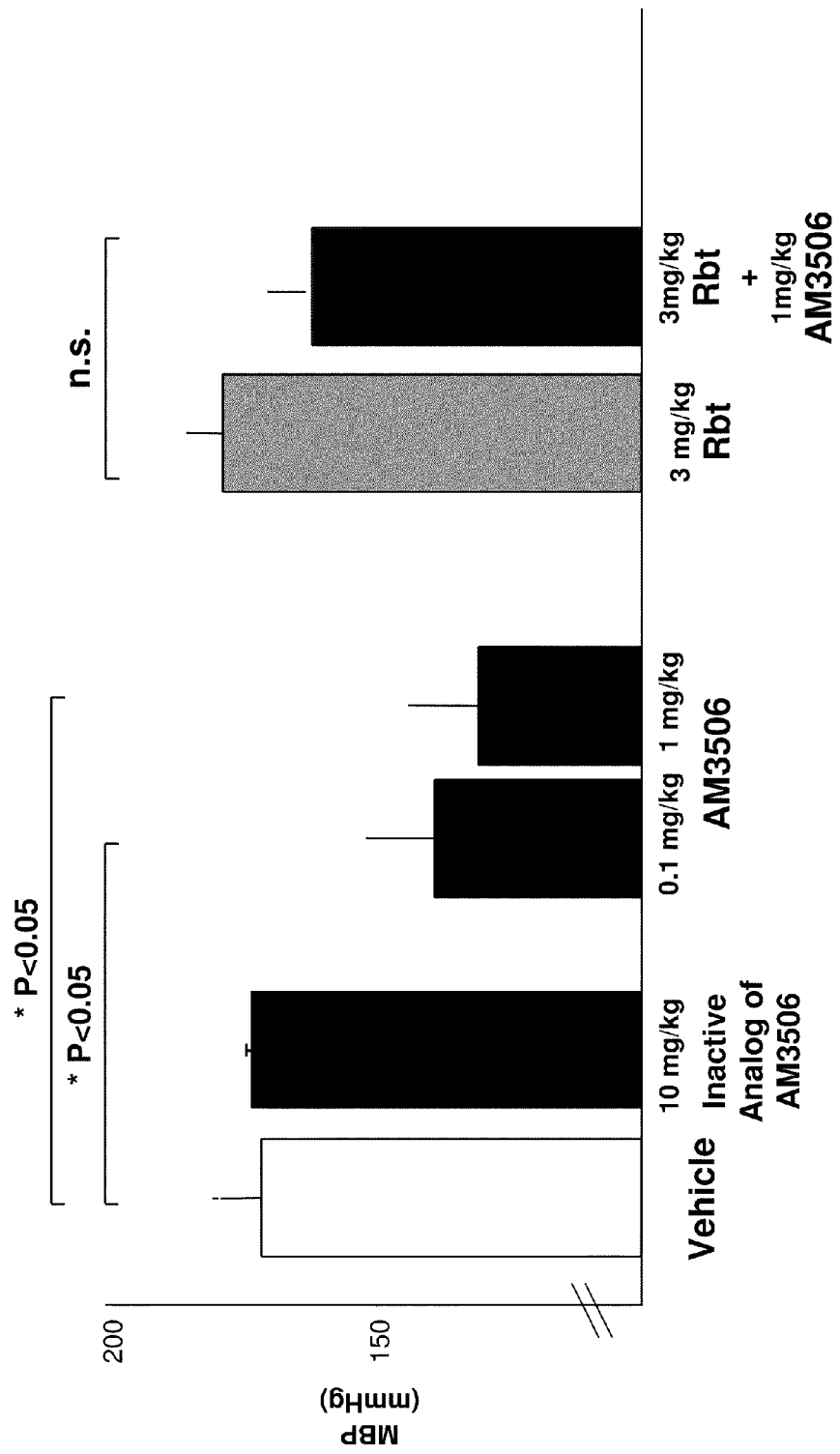
FIG. 6 is a bar graph charting mean blood pressure conscious SHR treated with the FAAH inhibitor AM3506, the $CB_1$ receptor antagonist rimonabant (Rbt), both AM3506 and Rbt, and an inactive control.
Figure 7:
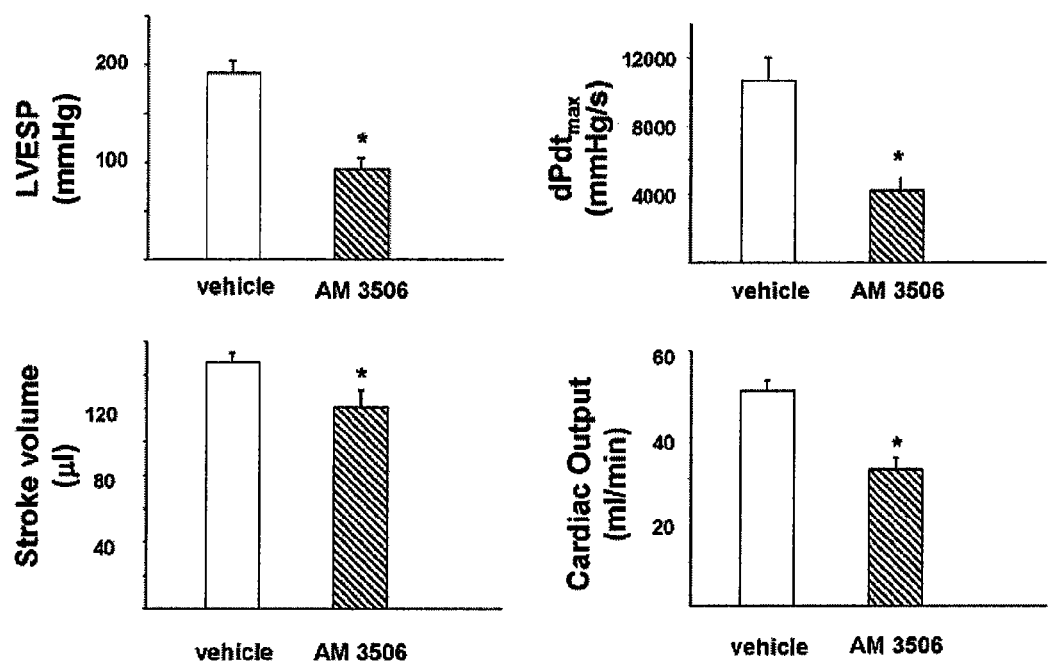
FIG. 7 is a series of bar graphs illustrating that in anesthetized SHR, a bolus dose of 1 mg/kg AM3506 significantly decreases the inappropriately increased cardiac contractility, as indicated by the decreases in left ventricular end systolic pressure (LVESP) and the decrease in the maximal slope of the systolic pressure increment (dP/dt), resulting in reduced stroke volume and cardiac output.

For the experiments illustrated in FIG. 3, FAAH activity was assessed through a different method not requiring TLC separation, as described by Jonsson et al: *Br. J. Pharmacol.* 133:1263-1275, 1997. Briefly, mice were treated in vivo with intraperitoneal injections of vehicle or different doses of AM3506 or URB597. The mice were sacrificed one hour later, the brain and liver removed, and tissue homogenates prepared as described above. [$^3$H]Anandamide labeled on the ethanolamide moiety was added to the homogenate and incubated at 37° C. for 10 min. The homogenate was then extracted twice with chloroform:methanol 1:1 and the radioactivity in the aqueous phase (containing the released ethanolamide) was counted.

Exemplary compounds exhibit inhibition of FAAH at concentrations less than 100 nM. Another exemplary assay for FAAH inhibition is disclosed in U.S. Pat. No. 6,699,682 to Gilula et al. (Gilula). The assay disclosed by Gilula is incorporated herein by reference.

Example 2

This example describes a general method for measuring analgesia induced by administration of the disclosed FAAH inhibitors. Compositions for administration of FAAH inhibitors are prepared by mixing the inhibitor with two parts Tween 80 by weight and dispersing into 0.9 w/v aqueous NaCl solution (saline) as described previously for $\Delta^9$-THC (Pertwee et al., *Br. J. Pharmacol.* 1992, 105, 980).

Drug mixtures are injected intravenously into male MF1 mice weighing 23-29 grams. Analgesia is measured by means of a "rat flick test" in which the time taken for a lightly restrained mouse to flick it tail away from a radiant heat stimulus is noted. The method is based on the test described by D'Amour and Smith (D'Amour, F. E., Smith, D. L., *J. Pharmacol. Exp. Ther.* 1941, 72, 74-79). Mice are subjected to the tail flick at −30 minutes (control latency) and at 12 minutes (test latency). The maximum possible tail flick latency is 10 seconds as mice that do not respond within this time are removed from the apparatus to prevent tissue damage. Analgesia is calculated as a percentage of maximum possible effect by expressing the ratio (test latency-control latency)/(10-control latency) as a percentage (Compton, D. R., et al., *J. Pharmacol. Exp. Ther.* 1992, 260, 2012-09). Ambient temperature is kept between 20 and 22° C. Values may be expressed as means and limits of error as standard errors. Dunnett's test may be used to calculate the significance of differences between the mean effect of each drug treatment and the mean effect of the vehicle, Tween 80.

Example 3

This example demonstrates that FAAH inhibitors reduce hypertension in hypertensive subjects but not in normotensive subjects. The results presented herein document tonic activation of cardiac and vascular $CB_1$ in hypertension that limits increases in blood pressure and cardiac contractility. They also indicate that upregulation of $CB_1$ is responsible for this tone and that increasing it by inhibiting the inactivation of endogenous anandamide can normalize blood pressure and cardiac contractile performance in hypertension.

As demonstrated herein, URB597, an inhibitor of FAAH that degrades anandamide in vivo, (Kathuria S et al., *Nature Medicine* 2003; 9, 76-81) increases brain levels of anandamide and unmasks tonic analgesia mediated by $CB_1$ Treatment of Wistar-Kyoto rats with URB597 (10 mg/kg IV) had no detectable hemodynamic effects, whereas in SHR, URB597 decreased arterial pressure to normotensive levels for >30 minutes and also decreased LV systolic pressure, dP/dt, and TPRI (results not shown). A maximally effective dose of URB597 was employed based on dose-response studies (n=3), which established its hypotensive ED50 at 1.7 mg/kg.

An URB597-induced decrease in cardiac contractility in SHR was also indicated by the change in pressure/volume relationship (not shown). URB597 similarly lowered blood pressure in angiotensin II-treated hypertensive rats but not in their normotensive controls. The effects of URB597 in the hypertensive animals could be prevented by $CB_1$ antagonists. MAP of SHR was also decreased by treatment with the anandamide transport inhibitors AM404 (10 mg/kg, −63±19 mm Hg, n=4) or OMDM-2 (5 mg/kg, −39±10 mm Hg, n=4), which increase anandamide levels at the receptor by blocking its cellular uptake, whereas no significant change was observed in Wistar-Kyoto rats.

Hypertensive rats also exhibited increased sensitivity to $CB_1$ agonists, and the effects of URB597 were remarkably similar to those of exogenous anandamide. In Wistar-Kyoto rats, anandamide (10 mg/kg) caused a modest and short-lasting (<5 minutes) decrease in blood pressure and cardiac contractility, without other hemodynamic changes. In SHR, the same dose of anandamide caused a sustained decrease in blood pressure to near normotensive levels, accompanied by decreases in heart rate, cardiac contractility (dP/dt, LV systolic pressure), CI, and TPRI. The cardiac pressure-volume effects of anandamide were similar to those of URB597, and anandamide-induced hypotension was potentiated in rats with angiotensin II-induced hypertension. The effects of the synthetic CB agonist HU210 were similarly potentiated, with its hypotensive EC50 reduced from 5.9 to 1.5 µg/kg and its maximal hypotensive effect increased from −39±14 to −108±11 mm Hg in Wistar-Kyoto rats (n=6) versus SHR (n=6, P<0.01), respectively.

Because anandamide is a known ligand for vanilloid receptors (VR1), the ability of the VR1 antagonist capsazepine to inhibit the hypotensive response to URB597 or anandamide in SHR was evaluated. The hypotensive response to either agent was not affected by capsazepine pretreatment (data not shown).

Example 4

This example describes a general protocol for the preparation of alkylsulfonyl fluoride FAAH inhibitors according to the scheme:

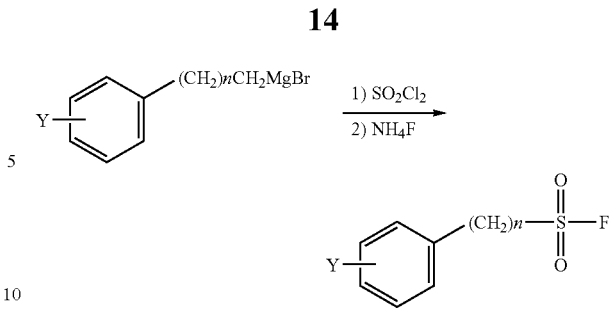

With reference to the scheme above, alkylmagnesium bromide in dry ether was added to a stirred solution of sulfuryl chloride (2-fold excess) in hexane at 0° C. The reaction mixture was stirred for 1 hour at 0° C. and then the ice bath was removed and stirring was continued overnight at room temperature. The solvent was evaporated in vacuo and the product was purified via column chromatography on silica gel to afford the corresponding alkylsulfonyl chloride as white solid. Alkylsulfonyl chloride was dissolved in acetone and a 10-fold excess of ammonium fluoride was added while stirring at room temperature. The reaction mixture was refluxed for 3 hours. The mixture was filtered to remove the insoluble salt, the solvent was evaporated and the product was dried in vacuo. Water was added to hydrolyze any unreacted alkylsulfonyl chloride and the aqueous mixture was extracted with ether. The ethereal extracts were combined, dried, filtered and the solvent was removed in vacuo. The product was purified with column chromatography on silica gel to afford the corresponding alkylsulfonyl fluoride.

Example 5

Male C57Bl6/J mice, wild-type or liver-specific $CB_1$ receptor knockout, were kept on a diet containing 60% of calories as fat (Research Diets Inc) for 14 weeks, by which time both strains have become fat due to increased adipose mass. Mice were then fasted overnight, followed by an i.p. injection of vehicle, 10 mg/kg URB597 or 1 mg/kg AM3506. Sixty minutes later the mice received 1.5 g/kg glucose i.p. and blood glucose levels were monitored for 2 hours.

Figure 8:
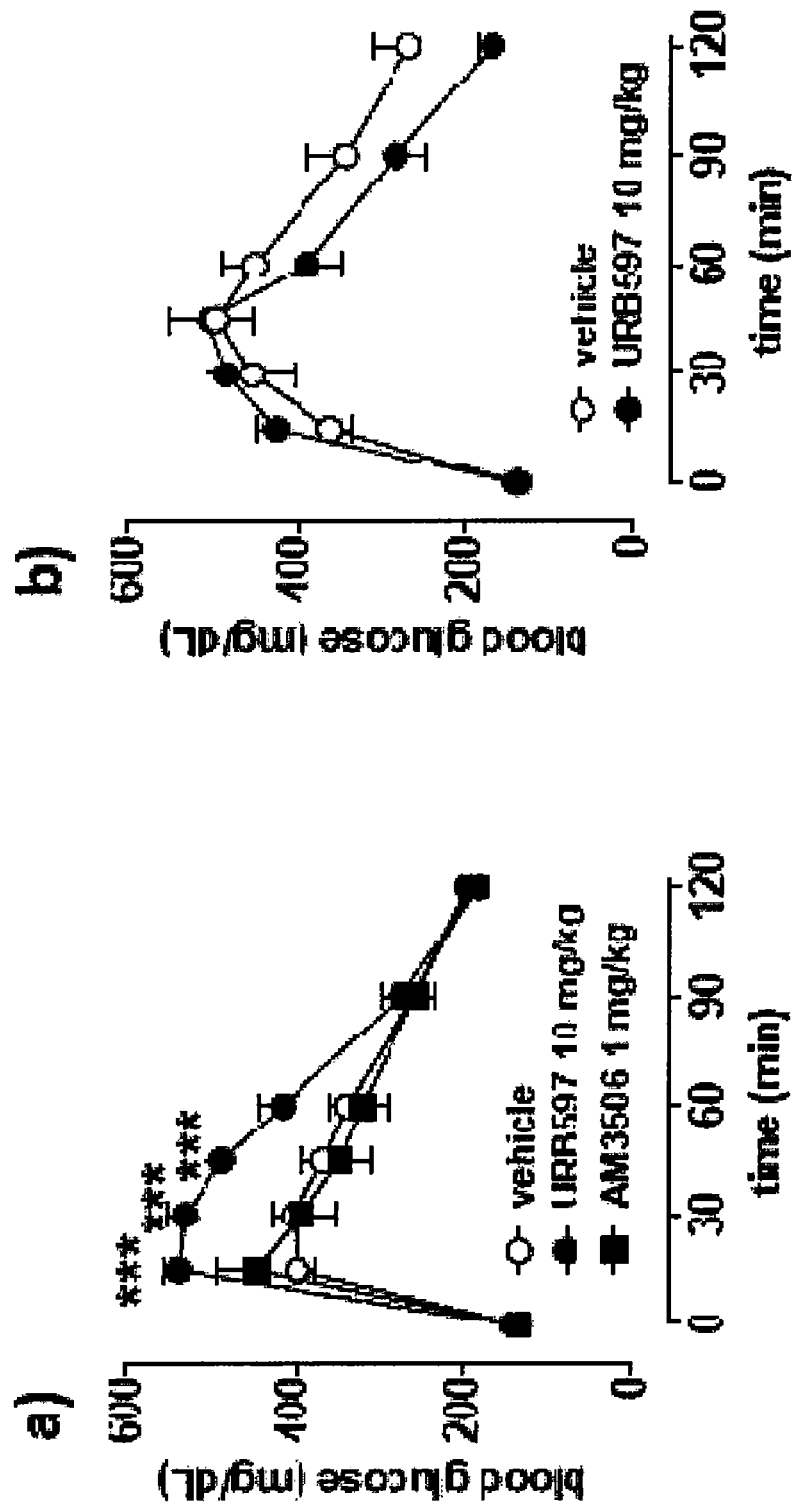
FIG. 8 is two graphs illustrating that URB597, but not AM3506, increases glucose intolerance in mice with diet-induced obesity. a) Male wild-type (a) or liver-specific $CB_1$ knockout mice (b), kept on a high-fat diet for 14 weeks, were subjected to an intraperitoneal glucose tolerance test 60 min following the i.p. injection of vehicle, 10 mg/kg URB597 or 1 mg/kg AM3506. Values are means±s.e.m from 4-11 experiments. *P<0.001, P<0.01 compared to vehicle.

High-fat diet (HFD)-induced obesity (DIO) is associated with increased activity of the hepatic endocannabinoid/$CB_1$ receptor system, which contributes to obesity-related glucose intolerance/insulin resistance. Tests were conducted to determine whether acute treatment with FAAH inhibitors can influence glycemic control in DIO mice. As illustrated in FIG. 8a, treatment of male DIO mice with 10 mg/kg URB597, a dose that significantly inhibits FAAH activity in the liver, resulted in a marked increase in their glucose intolerance (AUC increased from 322±37 to 464127 mg h/dL, n=11, P<0.05), where treatment of DIO mice with 1 mg/kg AM3506, a dose equieffective with 10 mg/kg URB597 in producing hypotension and inhibition of FAAH in brain but devoid of inhibitory potency in liver, had no such effect (AUC 343±50 mg h/dL, n=7). Furthermore, similar treatment with URB597 failed to affect glucose tolerance in liver-specific $CB_1$ receptor knockout mice kept on HFD (FIG. 8b, AUC 480±62 on vehicle vs 422±59 mg h/dL on URB597, n=4). These findings indicate that blockade of FAAH in liver results in hepatic $CB_1$ receptor-mediated increase in glucose intolerance.

URB597 (10 mg/kg i.p.) also increased non-fasting blood glucose in both SHR (from 104.0±7.4 to 144.0±9.6 mg/dL, n=4, P<0.05) and WKY (from 90.0±7.2 to 135.3±12.9 mg/dL, n=4, P<0.05) whereas AM3506, 1 mg/kg i.p., had no such effect (SHR: 97.8±5.6 to 97.8±2.9, n=6; WKY: 114.5±5.3 to 108.2±4.5, n=6). In the same mice, 10 mg/kg URB597 blocked hepatic FAAH activity by 93.1±0.3% in SHR and 92.6±0.2% in WKY, whereas 1 mg/kg AM3506 only marginally reduced it, by 11.1±0.04% in SHR and 6.7±0.2% in WKY (n=3-5).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of treating hypertension in a subject, comprising treating the subject with a therapeutically effective amount of compound of the formula Ar—R-E wherein Ar is an optionally substituted aryl or heteroaryl group;
R is an aliphatic linker group; and
E comprises at least one moiety selected from a trifluoromethyl ketone, boronic acid, boronic acid ester, fluorosulfone, fluorophosphonate, α-haloketone and α-ketoester.

2. The method of claim 1, wherein the treatment does not elicit hyperglycemia in the subject.

3. The method of claim 1, wherein the treatment does not increase glucose intolerance in the subject.

4. The method of claim 1, wherein E is selected from fluorosulfone and fluorophosphonate moieties.

5. The method of claim 1, wherein R represents $(CH_2)_n$ and n is from 2 to 20.

6. The method of claim 5, wherein n is from 2 to 10.

7. The method of claim 1, wherein Ar has the formula

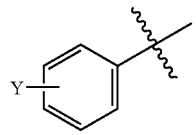

wherein Y is selected from —$OR^1$, —$NR^2R^3$ and halogen; and
$R^1$, $R^2$ and $R^3$ independently are selected from H, lower alkyl, acyl and aralkyl.

8. The method of claim 1, wherein the compound has the formula

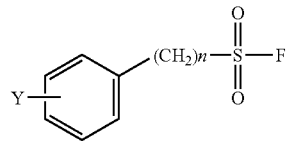

wherein Y is selected from —$OR^1$, —$NR^2R^3$ and halogen;
$R^1$, $R^2$ and $R^3$ are independently selected from H, lower alkyl, acyl and aralkyl; and
n is from about 2 to about 10.

9. The method of claim 8, wherein Y is —$OR^1$.

10. The method of claim 1, wherein the compound has the formula

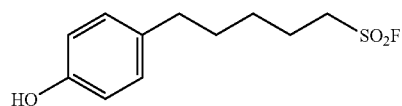

11. The method of claim 1, wherein the compound has an FAAH inhibitory concentration of less than about 250 nM.

12. The method of claim 1, wherein the compound has an FAAH inhibitory concentration of from about 1 nM to about 50 nM.

13. The method of claim 1, wherein the compound has an FAAH inhibitory concentration of from about 250-fold to about 1,000-fold lower than its MGL inhibitory concentration.

14. The method of claim 1, wherein the compound has an affinity for the $CB_1$ receptor of less than about 5,000 nM.

* * * * *